(12) United States Patent
Aizenfeld et al.

(10) Patent No.: US 12,207,796 B2
(45) Date of Patent: *Jan. 28, 2025

(54) MULTI-JET CONTROLLER FOR AN ENDOSCOPE

(71) Applicant: EndoChoice Inc., Alpharetta, GA (US)

(72) Inventors: Amram Aizenfeld, Ramot Menashe (IL); Golan Salman, Atlit (IL); Hadar Schwarcz, Netanya (IL)

(73) Assignee: EndoChoice Inc., Alpharetta, GA (US)

(*) Notice: Subject to any disclaimer, the term of this patent is extended or adjusted under 35 U.S.C. 154(b) by 189 days.

This patent is subject to a terminal disclaimer.

(21) Appl. No.: 17/837,217

(22) Filed: Jun. 10, 2022

(65) Prior Publication Data

US 2022/0296086 A1 Sep. 22, 2022

Related U.S. Application Data

(63) Continuation of application No. 16/743,717, filed on Jan. 15, 2020, now Pat. No. 11,375,885, which is a
(Continued)

(51) Int. Cl.
*A61B 1/015* (2006.01)
*A61B 1/00* (2006.01)
*F04B 43/12* (2006.01)

(52) U.S. Cl.
CPC .......... *A61B 1/015* (2013.01); *A61B 1/00096* (2013.01); *A61B 1/00101* (2013.01);
(Continued)

(58) Field of Classification Search
CPC ............ A61B 1/00105; A61B 1/00091; A61B 1/00119; A61B 1/00128; A61B 1/00137; F04B 43/086; F04B 43/12; F04C 14/04
(Continued)

(56) References Cited

U.S. PATENT DOCUMENTS 3,639,714 A 2/1972 Fujimoto
3,955,064 A 5/1976 Demetrio
(Continued)

FOREIGN PATENT DOCUMENTS

CA 2297986 3/1999
CA 2765559 12/2010
(Continued)

OTHER PUBLICATIONS

Corrected Notice of Allowance dated Apr. 13, 2016 for U.S. Appl. No. 13/680,646.
(Continued)

*Primary Examiner* — Aaron B Fairchild
(74) *Attorney, Agent, or Firm* — Bookoff McAndrews PLLC

(57) ABSTRACT

The present specification describes a control mechanism to control fluid flow through one or more fluid channels that supply fluid to the distal tip of an endoscope. A pump is provided with an endoscope to control the flow of fluid from an external source to a combination of fluid channels within the endoscope, which supply fluid to front and side jets of a multi-jet endoscope assembly. The pump is preferably dual-direction pump that enables control of fluid to either the front jet or to the front and side jets of the endoscope.

14 Claims, 10 Drawing Sheets

Related U.S. Application Data continuation of application No. 15/439,782, filed on Feb. 22, 2017, now Pat. No. 10,595,714, which is a continuation-in-part of application No. 14/469,501, filed on Aug. 26, 2014, now Pat. No. 9,993,142, and a continuation-in-part of application No. 14/317,863, filed on Jun. 27, 2014, now Pat. No. 9,636,003, and a continuation-in-part of application No. 14/229,699, filed on Mar. 28, 2014, now Pat. No. 9,642,513.

(60) Provisional application No. 62/340,121, filed on May 23, 2016, provisional application No. 61/910,863, filed on Dec. 2, 2013, provisional application No. 61/840,706, filed on Jun. 28, 2013, provisional application No. 61/812,709, filed on Apr. 16, 2013, provisional application No. 61/806,065, filed on Mar. 28, 2013.

(52) U.S. Cl.
CPC ...... *A61B 1/00105* (2013.01); *A61B 1/00119* (2013.01); *A61B 1/00128* (2013.01); *F04B 43/12* (2013.01); *A61B 1/00091* (2013.01); *A61B 1/00103* (2013.01); *A61B 1/00137* (2013.01)

(58) Field of Classification Search
USPC ......... 417/474, 476, 477.1; 137/112, 119.01, 137/265, 565.26, 565.33, 614.2
See application file for complete search history.

(56) References Cited

U.S. PATENT DOCUMENTS

| | | |
|---|---|---|
| 4,027,697 A | 6/1977 | Bonney |
| 4,037,588 A | 7/1977 | Heckele |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Garashi |
| 4,984,878 A | 1/1991 | Miyano |
| 5,007,406 A | 4/1991 | Takahashi |
| 5,014,685 A | 5/1991 | Takahashi |
| 5,191,878 A | 3/1993 | Iida et al. |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | Mckenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | Mckenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | EbbesmeierneeSchitthof |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | Mckenna |
| 6,277,064 B1 | 8/2001 | Yoon |
| 6,309,347 B1 | 10/2001 | Takahashi et al. |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | Mayerlll |
| 6,712,760 B2 | 3/2004 | Sano |
| 6,832,984 B2 | 12/2004 | Stelzer |
| 6,888,119 B2 | 5/2005 | Iizuka |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,881,752 B1 | 11/2014 | Fonteyn |
| 8,926,502 B2 | 1/2015 | Levy |
| 9,044,185 B2 | 6/2015 | Bayer |
| 9,101,266 B2 | 8/2015 | Levi |

(56) References Cited

U.S. PATENT DOCUMENTS

| | | |
|---|---|---|
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0106285 A1 | 5/2006 | Boulais et al. |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0276689 A1 | 12/2006 | Litscher |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | Mccutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0265498 A1 | 11/2007 | Ito |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0209811 A1 | 8/2009 | Higuchi |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |

(56) References Cited

U.S. PATENT DOCUMENTS

| | | |
|---|---|---|
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0224654 A1 | 9/2011 | Schulz |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0088974 A1 | 4/2012 | Maurice |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |

(56) References Cited

FOREIGN PATENT DOCUMENTS

| | | |
|---|---|---|
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H06-142029 A | 5/1994 |
| JP | H1043129 | 2/1998 |
| JP | H10239740 | 9/1998 |
| JP | 11137512 | 5/1999 |
| JP | H11-244221 A | 9/1999 |
| JP | 2002-238906 A | 8/2002 |
| JP | 2005253543 | 9/2005 |
| JP | 2006025888 | 2/2006 |
| JP | 2006068109 | 3/2006 |
| JP | 2009-536552 A | 10/2009 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| JP | 7046837 B2 | 4/2022 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2009095915 A1 | 8/2009 |
| WO | 2010146587 A1 | 12/2010 |
| WO | 2012038958 | 3/2012 |
| WO | 2012056453 A2 | 5/2012 |
| WO | 2012075153 A2 | 6/2012 |
| WO | 2012077116 | 6/2012 |
| WO | 2012077117 A1 | 6/2012 |
| WO | 2012096102 | 7/2012 |
| WO | 2012120507 A1 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2015/198696 A1 | 12/2015 |
| WO | 2016014581 | 1/2016 |
| WO | 2016033403 | 3/2016 |

OTHER PUBLICATIONS

Notice of Allowance dated Mar. 28, 2016 for U.S. Appl. No. 13/413,059.
Notice of Allowance dated Mar. 29, 2016 for U.S. Appl. No. 13/680,646.
Office Action date Feb. 26, 2016 for U.S. Appl. No. 14/274,323.
Office Action dated Feb. 4, 2016 for U.S. Appl. No. 14/271,234.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, June 2001—article obtained online from http://www.ptonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.

(56) References Cited

OTHER PUBLICATIONS

Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action mailed Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/500,975.
International Search Report for PCT/US14/37004, Sep. 25, 2014.
International Search Report for PCT/US14/38094, Nov. 6, 2014.
International Search Report for PCT/US2014/037526, Oct. 16, 2014.
International Search Report for PCT/US2014/071085, mailed on Mar. 27, 2015.
International Search Report for PCT/US2014/58143, mailed on Jan. 21, 2015.
International Search Report for PCT/US2015/012506, mailed on Dec. 11, 2015.
International Search Report for PCT/US2015/012751, mailed on Jun. 26, 2015.
International Search Report for PCT/US2015/027902, mailed on Jul. 23, 2015.
International Search Report for PCT/US2015/28962, mailed on Jul. 28, 2015.
International Search Report for PCT/US2015/29421, mailed on Aug. 7, 2015.
International Search Report for PCT/US2015/41396, mailed on Sep. 29, 2015.
International Search Report for PCT/US2015/47334, mailed on Dec. 28, 2015.
International Search Report for PCT/US2015/6548, mailed on Feb. 26, 2016.
International Search Report for PCT/US2015/66486, mailed on Dec. 17, 2015.
International Search Report for PCT/US2017/018972, May 30, 2017.

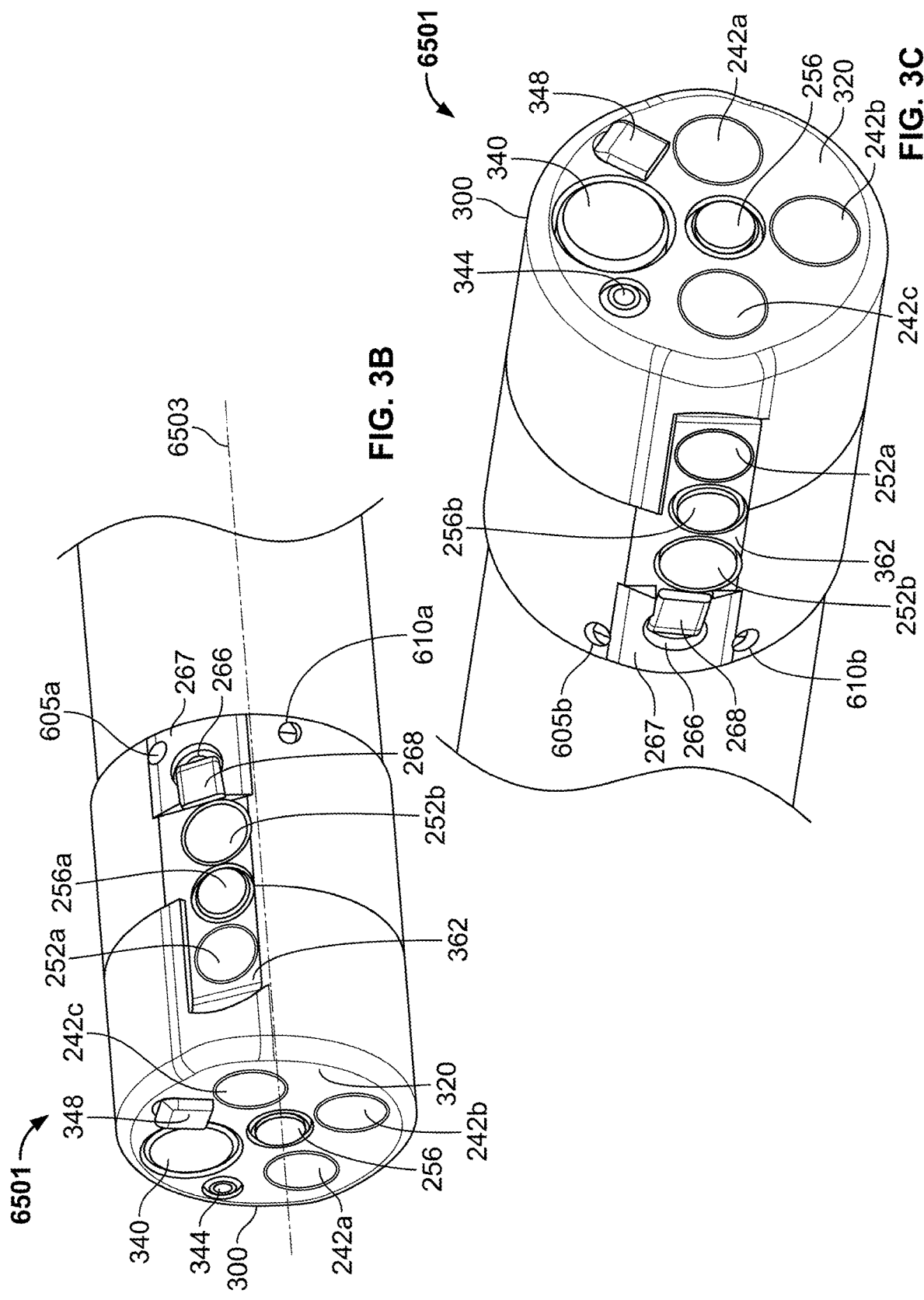

MULTI-JET CONTROLLER FOR AN ENDOSCOPE

CROSS-REFERENCE

This application is a continuation of U.S. Nonprovisional patent application Ser. No. 16/743,717, filed on Jan. 15, 2020, which claims the benefit of priority to U.S. Nonprovisional application Ser. No. 15/439,782, filed on Feb. 22, 2017, now U.S. Pat. No. 10,595,714, issued on Mar. 24, 2020, which claims the benefit of U.S. Provisional Application No. 62/340,121, filed on May 23, 2016, for priority.

The present application is also a continuation-in-part application of U.S. patent application Ser. No. 14/469,501, entitled "Fluid Distribution Device For A Multiple Viewing Elements Endoscope" and filed on Aug. 26, 2014, which, in turn, relies on U.S. Provisional Patent Application No. 61/910,863, entitled "Multi-Jet Endoscope" and filed on Dec. 2, 2013, for priority.

The present application is also a continuation-in-part application of U.S. patent application Ser. No. 14/317,863, entitled "Multi-Jet Distributor for An Endoscope" and filed on Jun. 27, 2014, which, in turn, relies on U.S. Provisional Patent Application No. 61/840,706, entitled "Multi-Jet Distributor For An Endoscope" and filed on Jun. 28, 2013, for priority.

The present application is also a continuation-in-part application of U.S. patent application Ser. No. 14/229,699 entitled "Compact Multi-Viewing Element Endoscope System", and filed on Mar. 28, 2014, which, in turn, relies on U.S. Provisional Patent Application No. 61/812,709, entitled "Multi Camera, Multi Jet Endoscope Having Two Side Service Channels" and filed on Apr. 16, 2013, and U.S. Provisional Patent Application No. 61/806,065, of the same title and filed on Mar. 28, 2013, for priority.

The present application also relates to U.S. patent application Ser. No. 14/278,293, entitled "Multiple Viewing Elements Endoscope Having Two Front Service Channels" and filed on May 15, 2014.

All of the above-mentioned applications are herein incorporated by reference in their entirety.

FIELD

The present specification generally relates to an endoscope assembly comprising a front jet and at least one side jet being supplied with fluid via fluid channels and a system to control direction of flow of fluid through the jets.

BACKGROUND

Endoscopes provide a means for performing medical procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular element to enable direct viewing of the patient's anatomy. Various surgical tools may be inserted through a working channel in the endoscope for performing different surgical procedures.

Endoscopes, such as colonoscopes, gastroscopes and the like, that are currently being used, typically have a front camera for viewing internal organs, such as the colon, an illuminator, a fluid injector for cleaning the camera lens, and a working channel for inserting surgical tools in order to, for example, remove polyps found in the colon. Often, endoscopes also have fluid ("jet") injectors for cleaning a body cavity, such as the colon, into which they are inserted.

There is a need in the art for endoscopes which enable the concurrent, and multi-directional, supply of fluids to multiple fluid injectors or jet openings in the endoscope tip in order to quickly and efficiently clean a body cavity or a portion of the endoscope.

SUMMARY

The following embodiments and aspects thereof are described and illustrated in conjunction with systems, tools and methods, which are meant to be exemplary and illustrative, not limiting in scope.

The present specification discloses an apparatus for controlling a flow direction of fluid from a fluid source external to an endoscope into a plurality of fluid channels positioned within a distal end of the endoscope, comprising: a tube comprising a first combination of fluid channels and a second combination of fluid channels; a pump connected to the tube, wherein the pump is adapted to direct fluid from the external source to at least one of a first combination of fluid channels and a second combination of fluid channels in said tube; and a controller to activate the pump, wherein the controller is configured to cause the pump to direct fluid to the first combination of fluid channels upon a first activation of the controller and wherein the controller is configured to cause the pump to direct fluid to the second combination of fluid channels upon a second activation of the controller.

Optionally, the pump is a peristaltic pump.

Optionally, the apparatus of further comprises a user trigger to control said controller, wherein the user trigger comprises a button and wherein the button is configured such that pressing the button causes the first activation of the controller and pressing the button twice causes the second activation of the controller.

Optionally, the apparatus further comprises a user trigger to control said controller, wherein the user trigger comprises a lever and wherein the lever is configured such that pulling the lever causes the first activation of the controller and pushing the lever causes the second activation of the controller.

Optionally, the apparatus further comprises a user trigger to control said controller, wherein the user trigger comprises a pedal and wherein the pedal is configured such that stepping on the pedal causes the first activation of the controller and stepping on the pedal twice causes the second activation of the controller.

Optionally, the first combination of fluid channels and the second combination of fluid channels are co-linearly placed within the tube.

The first combination of fluid channels may comprise a fluid channel that opens through a front jet in a distal tip of the endoscope.

The second combination of fluid channels may comprise a fluid channel that opens through a front jet in a distal tip of the endoscope and at least one side jet in the distal tip of the endoscope.

Optionally, the pump is configured to direct fluid in a first direction through the first combination of fluid channels upon said first activation of the controller, the pump is configured to direct fluid in a second direction through the second combination of fluid channels upon said second activation of the controller, and the first direction is different from the second direction.

Optionally, the apparatus further comprises a first check valve in a first fluid channel positioned between said external source and the pump and a second check valve in a second fluid channel positioned between said external source and the pump, wherein the first fluid channel is separate from the second fluid channel. Optionally, the first fluid channel is in fluid communication with the first combination of fluid channels, the second fluid channel is in fluid communication with the second combination of fluid channels, the first fluid channel is not in fluid communication with the second combination of fluid channels, and the second fluid channel is not in fluid communication with the first combination of fluid channels.

The present specification also discloses a method for controlling a flow direction of fluid from a fluid source external to an endoscope into a plurality of fluid channels positioned within the endoscope, comprising: receiving a user input into a trigger; based upon said trigger, using a controller to activate a pump connected to a tube, wherein said tube comprises a first combination of fluid channels and a second combination of fluid channels, wherein, upon a first activation of the pump, said pump causes fluid to flow in a first direction from the external source to the first combination of fluid channels, and wherein, upon a second activation of the pump, said pump causes fluid to flow in a second direction from the external source to the second combination of fluid channels.

Optionally, the pump comprises a peristaltic pump.

Optionally, said trigger comprises a button, wherein pressing the button once enables said first activation of the pump, and wherein pressing the button twice enables the second activation of the pump.

Optionally, said trigger comprises a lever, wherein pulling the lever enables the first activation of the pump and wherein pushing the lever enables the second activation of the pump.

Optionally, said trigger comprises a lever, wherein pulling or pushing the lever once enables the first activation of the pump and wherein pushing or pulling the lever twice enables the second activation of the pump.

Optionally, said trigger comprises a pedal, wherein pushing the pedal once causes the first activation of the pump and wherein pushing the pedal twice causes the second activation of the pump.

Optionally, the first combination of fluid channels and the second combination of fluid channels are co-linearly placed within the tube.

The first combination of fluid channels may comprise a fluid channel that opens through a front jet in a distal tip of the endoscope.

The second combination of fluid channels may comprise a fluid channel that opens through a front jet in a distal tip of the endoscope and at least one side jet in the distal tip of the endoscope.

Optionally, the pump is configured to direct fluid in a first direction through the first combination of fluid channels upon said first activation of the pump, the pump is configured to direct fluid in a second direction through the second combination of fluid channels upon said second activation of the pump, and the first direction is different from the second direction.

Optionally, a first check valve is included in a first fluid channel positioned between said external source and the pump and a second check valve is included in a second fluid channel positioned between said external source and the pump, wherein the first fluid channel is separate from the second fluid channel. Optionally, the first fluid channel is in fluid communication with the first combination of fluid channels, the second fluid channel is in fluid communication with the second combination of fluid channels, the first fluid channel is not in fluid communication with the second combination of fluid channels, and the second fluid channel is not in fluid communication with the first combination of fluid channels.

The present specification also discloses a system for controlling a flow direction of fluid from a source external to an endoscope into a plurality of fluid channels positioned within the endoscope, comprising: a pump, wherein the pump is adapted to direct fluid from the external source to at least a first combination of fluid channels and a second combination of fluid channels; an activation system to activate the pump, wherein the pump directs fluid to the first combination of fluid channels upon a first activation by the activation system and the pump directs fluid to the second combination of fluid channels upon a second activation by the activation system; and at least one check valve connected in the plurality of fluid channels to control the flow of fluid during the first activation and the second activation.

Optionally, the activation system comprises a button, wherein the first activation comprises pressing the button once and the second activation comprises pressing the button twice.

Optionally, the activation system comprises a lever, wherein the first activation comprises pulling the lever and the second activation comprises pushing the lever.

Optionally, the activation system comprises a pedal, wherein the first activation comprises pushing the pedal once and the second activation comprises pushing the pedal twice.

Optionally, the pump is a peristaltic pump.

Optionally, the first combination of fluid channels comprises a fluid channel that opens through a front jet in a distal tip of the endoscope. Optionally, the second combination of fluid channels comprises a fluid channel that opens through a front jet in a distal tip of the endoscope and at least one side jet in the distal tip of the endoscope.

Optionally, the system further comprises at least one endoscope connector housing the plurality of endoscope fluid channels. Optionally, the at least one endoscope connector is positioned within the endoscope. Optionally, the at least one endoscope connector is positioned within a main control unit external to the endoscope.

The aforementioned and other embodiments of the present specification shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 3B illustrates a perspective first side view of the tip section of the multi jet endoscope assembly of FIG. 3A;

FIG. 3C illustrates a perspective second side view of the tip section of the multi jet endoscope assembly of FIG. 3A;

DETAILED DESCRIPTION

In an embodiment, a pump is provided with an endoscope to control the flow of fluid from an external source to a combination of fluid channels within the endoscope, which supply fluid to a front jet or to the front jet and at least one side jet of a multi-jet endoscope assembly. In embodiments, the pump is a dual-direction pump that enables control of fluid to either the front jet or to the front and side jets of the endoscope. In various embodiments, the fluid flow control system of the present specification is intended for operation with a multiple viewing elements endoscope similar to those described in U.S. patent application Ser. No. 14/278,293, entitled "Multiple Viewing Elements Endoscope Having Two Front Service Channels" and filed on May 15, 2014, which is herein incorporated by reference in its entirety.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

Figure 1:
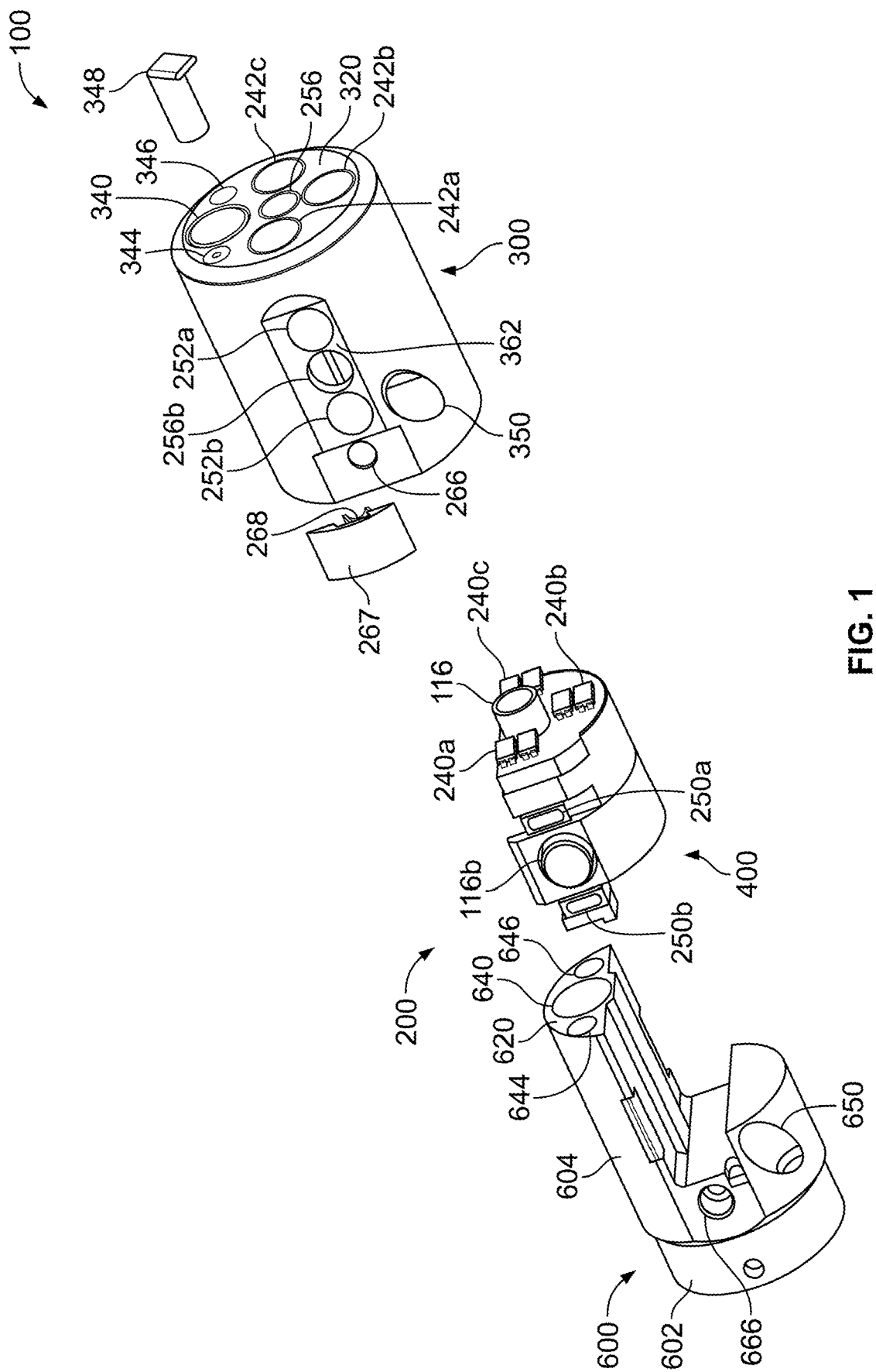
FIG. 1 illustrates an exploded view of a tip section of an endoscope assembly according to one embodiment of the present specification.

Reference is now made to FIG. 1, which shows an exploded view of a tip section 200 of a multi-viewing element endoscope assembly 100 comprising at least one front working/service channel, according to various embodiments. An aspect of some embodiments also relates to endoscope assembly 100 having the tip section 200 equipped with one or more side working/service channels.

It is noted that the term "endoscope" as mentioned to herein may refer particularly to a colonoscope or gastroscope, according to some embodiments, but is not limited only to colonoscopes and gastroscopes. The term "endoscope" may refer to any instrument used to examine the interior of a hollow organ or cavity of the body.

According to an embodiment, tip section 200 of endoscope 100 includes a tip cover 300, an electronic circuit board assembly 400 and a fluid channeling component 600.

According to some embodiments, fluid channeling component 600 may be configured as a separate component from electronic circuit board assembly 400. This configuration may be adapted to separate the fluid channels, at least one side service channel, such as side service channel 650, and at least one front working/service channel, such as working/service channel 640, which are located in fluid channeling component 600, from the sensitive electronic and optical parts which may be located in the area of electronic circuit board assembly 400. Thus, the component structure of the tip section 200 enables effective insulation of the plurality of electronic elements from the plurality of fluid channels.

Tip section 200 may be turnable by way of flexible shaft which is also referred to as a bending section, for example a vertebra mechanism.

In some embodiments, electronic circuit board assembly 400 is configured to carry a front viewing element 116 and at least one side viewing element 116b which may be similar to front viewing element 116 and may include a sensor such as but not limited to a Charge Coupled Device (CCD) or a Complementary Metal Oxide Semiconductor (CMOS) image sensor. In addition, electronic circuit board assembly 400 may be configured to carry a second side viewing element on the opposite side of side viewing element 116b, which may be similar to front viewing element 116 and may include a sensor such as but not limited to a Charge Coupled Device (CCD) or a Complementary Metal Oxide Semiconductor (CMOS) image sensor.

Electronic circuit board assembly 400 may further be configured to carry front illuminators 240a, 240b, 240c, which are, in one embodiment, associated with front viewing element 116 and are positioned to essentially illuminate the fields of view of front viewing element 116.

In addition, electronic circuit board assembly 400 may further be configured to carry side illuminators 250a and 250b, which are, in one embodiment, associated with side viewing element 116b and are positioned to essentially illuminate the fields of view of side viewing element 116b. Electronic circuit board assembly 400 may also be configured to carry side illuminators, which are associated with a second side viewing element that is positioned on the opposite side of side viewing element 116b, which may be similar to side illuminators 250a and 250b.

Front illuminators 240a, 240b, 240c and side illuminators 250a and 250b may optionally be discrete illuminators and may include a light-emitting diode (LED), which may be a white light LED, an infrared light LED, a near infrared light LED, an ultraviolet light LED or any other LED.

The term "discrete", concerning discrete illuminator, may refer to an illumination source, which generates light internally-in contrast to a non-discrete illuminator, which may be, for example, a fiber optic merely transmitting light generated remotely.

Figure 2A:
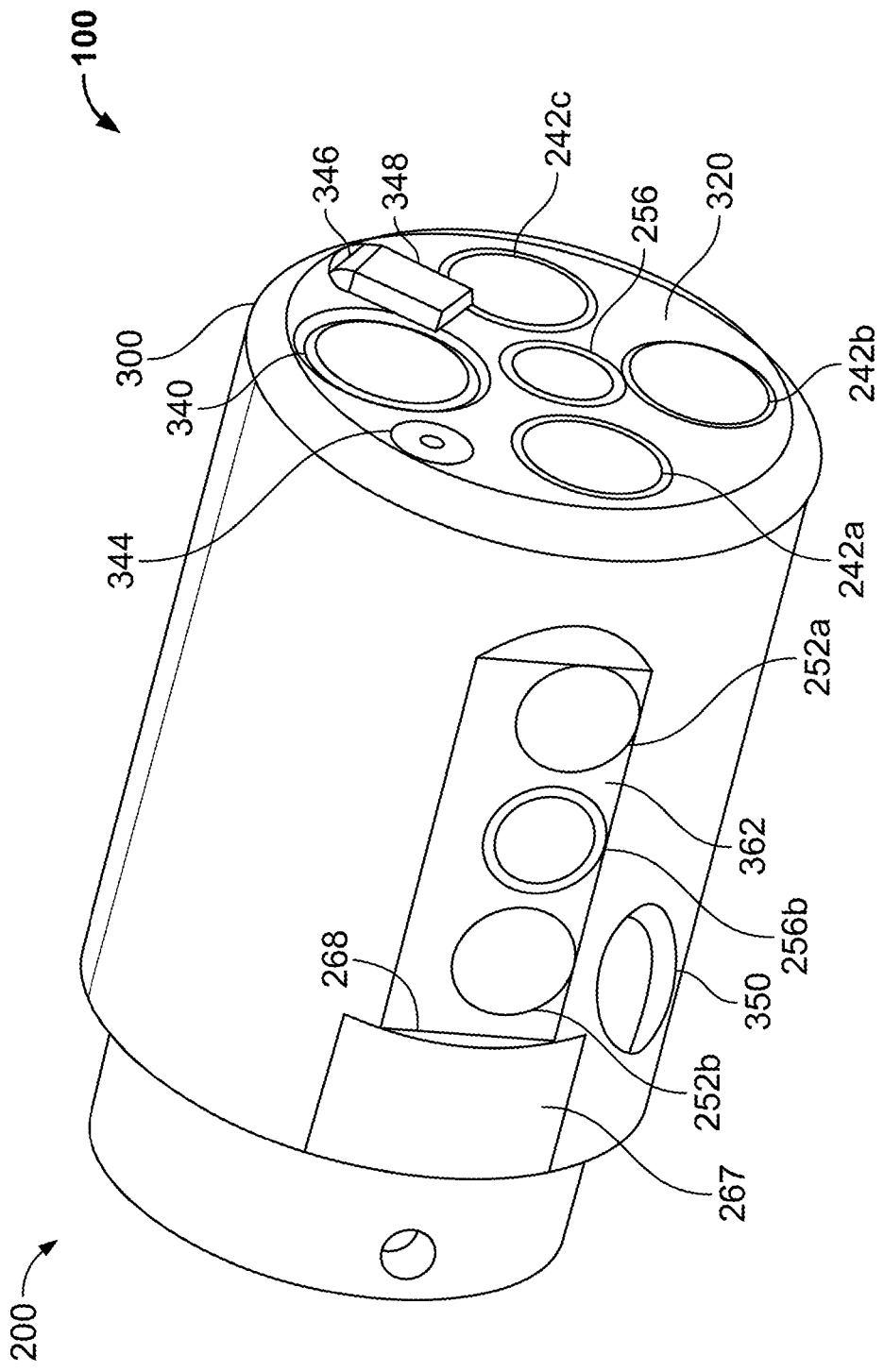
FIG. 2A illustrates a perspective view of a tip section of an endoscope assembly according to one embodiment of the present specification.
Figure 2B:
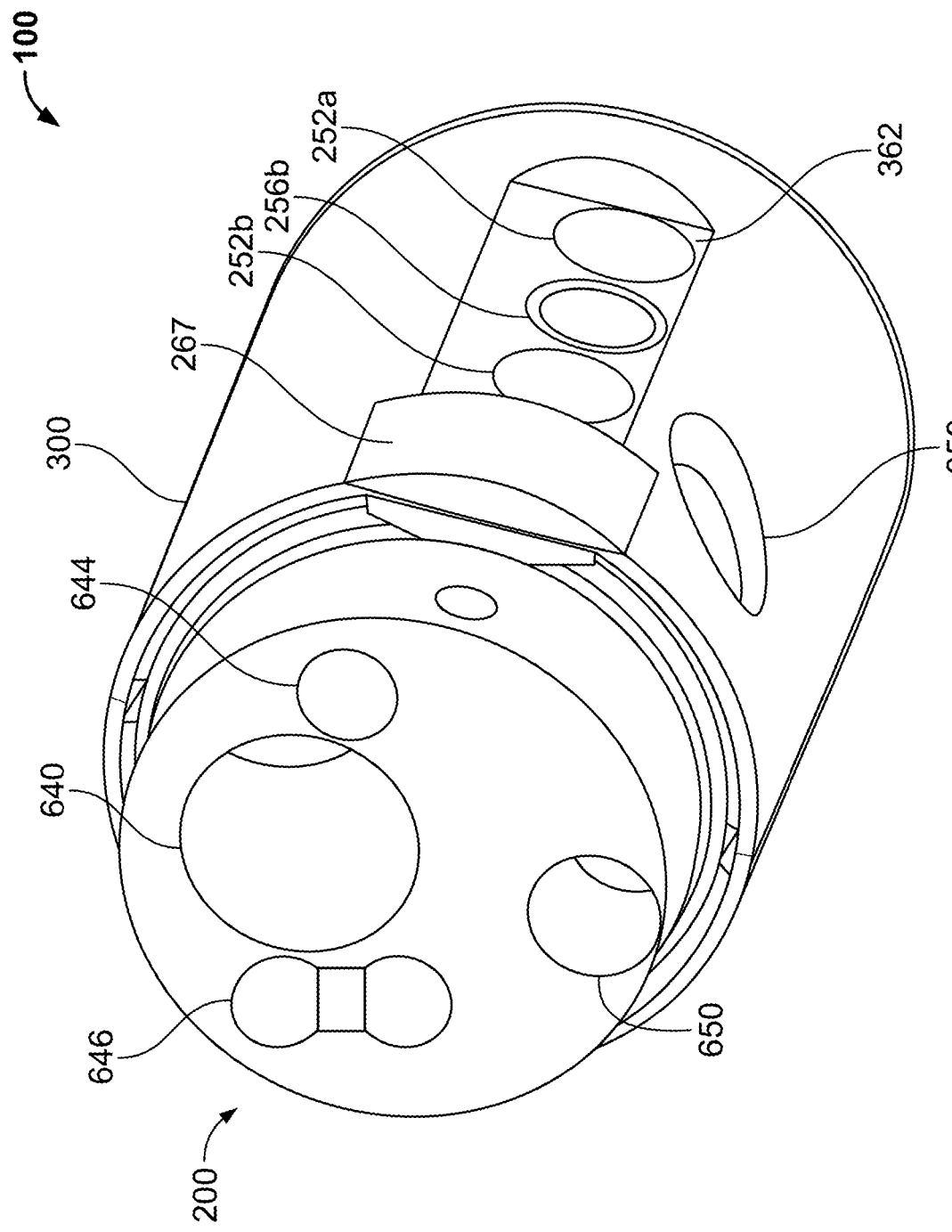
FIG. 2B illustrates another perspective view of a tip section of an endoscope assembly according to one embodiment of the present specification.

Reference is now made to FIG. 1 along with FIG. 2A and FIG. 2B, which show a perspective view of a tip section 200 of an endoscope assembly 100 according to an embodiment.

Tip cover 300 may be configured to fit over the inner parts of the tip section 200 including electronic circuit board assembly 400 and fluid channeling component 600 and to provide protection to the internal components in the inner parts.

Tip cover 300 may include a front panel 320 having a transparent surface, window, or opening for front optical lens assembly 256, of front looking camera or viewing element 116. Front optical lens assembly 256 may include a plurality of lenses, static or movable, which may provide a field of view of 90 degrees or more, 120 degrees or more or up to essentially 180 degrees. Front optical lens assembly 256 may provide a focal length in the range of about 3 to 100 millimeters.

An optical axis of front looking camera or viewing element 116 may be essentially directed along the long dimension of the endoscope. However, since front viewing element 116 is typically a wide angle viewing element, its field of view may include viewing directions at large angles to its optical axis. Additionally, front panel 320 may include optical windows 242a, 242b and 242c of illuminators 240a, 240b and 240c, respectively. It should be noted that number of illumination sources used for illumination of the field of view may vary.

In addition, front panel 320 may include a working channel opening 340 of a working channel 640. In alternate embodiments, the front panel may include more than one working channel opening.

Jet channel opening 344 of jet channel 644 may also be located on front panel 320 of tip cover 300. Jet channel 644 may be configured for providing high-pressure jet of fluid such as water or saline for cleaning the walls of the body cavity.

Also located on front panel 320 of tip cover 300 is injector opening 346 of injector channel 646 having a nozzle 348 aimed at front optical lens assembly 256. Injector channel 646 may be configured for injecting fluid (liquid and/or gas) to wash contaminants such as blood, feces and other debris from a surface of front optical lens assembly 256 of front viewing element 116. Optionally, injector channel 646 may be configured for cleaning front optical lens assembly 256 and one, two, or all of optical windows 242a, 242b and 242c. Injector channel 646 may be fed by fluid such as water and/or gas which may be used for cleaning and/or inflating a body cavity.

Visible on the sidewall 362 of tip cover 300 is side optical lens assembly 256b for side viewing element 116b, which may be similar to front optical lens assembly 256 and optical windows 252a and 252b of illuminators 250a and 250b for side viewing element 116b. Also on the sidewall 362 of tip cover 300, on the opposing side of first side optical lens assembly 256b, is a second optical lens assembly for a second side viewing element, which may be similar to side optical lens assembly 256b and optical windows 252a and 252b of illuminators 250a and 250b for side viewing element 116b. The first side optical lens assembly 256b may provide a focal length in the range of about 3 to 100 millimeters.

An optical axis of the first side viewing element 116b may be essentially directed perpendicular to the long dimension of the endoscope. An optical axis of the second side viewing element may be essentially directed perpendicular to the long dimension of the endoscope. However, since each side viewing element typically comprises a wide angle camera, its field of view may include viewing directions at large angles to its optical axis. In accordance with some embodiments, each side viewing element has a field of view of 90 degrees or more, 120 degrees or more or up to essentially 180 degrees.

In addition, side injector opening 266 of side injector channel 666 may be located at distal end of sidewall 362. A nozzle cover 267 may be configured to fit side injector opening 266.

Additionally, nozzle cover 267 may include a nozzle 268 which may be aimed at side optical lens assembly 256b and configured for injecting fluid to wash contaminants such as blood, feces and other debris from a surface of side optical assembly 256b of side viewing element 116b. The fluid may include gas which may be used for inflating a body cavity. Optionally, nozzle 268 may be configured for cleaning both side optical lens assembly 256b and optical windows 252a and/or 252b.

According to some embodiments, side injector channel 666 may be configured to supply fluids for cleaning any of the tip elements (such as any optical assembly, optical lens assembly, windows, illuminators, and other elements).

Optionally, injector channel 646 and side injector channel 666 may be fed from same channel.

It is noted that according to some embodiments, although tip section 200 is presented herein showing one side thereof, the opposing side may include elements similar to the side elements described herein (for example, side viewing element, side optical lens assembly, injector(s), nozzle(s), illuminator(s), window(s), opening(s) and other elements).

Sidewall 362 may have a form of an essentially flat surface which assists in directing the cleaning fluid injected from injector channel 666 towards side optical lens assembly 256b and optical windows 252a and/or 252b. Lack of such flat surface may result in dripping of the cleaning fluid along the curved surface of tip section 200 of the endoscope without performing the desired cleaning action.

In accordance with an embodiment, the sidewall 362 is located in a notch/depression in the tip cover 300. This way, side injector opening 266 and corresponding side nozzle 268 may be elevated from the depressed sidewall 362 but still not significantly protrude from the level of cylindrical surface of the tip cover 300. According to an aspect of one embodiment, as shown in FIG. 59C, the sidewall 362 is located in a sufficiently well-defined or deep notch/depression 5963 in the tip cover 300 such that the lens assembly of side optical lens assembly 256b stays sufficiently embedded in the notch/depression 363 and well below the level 5900 of the cylindrical surface of the tip cover 300. The notch/depression 5963 protects the sidewall 362 and components thereof (side optical lens assembly 256b, side illuminators 250a, 250b and side nozzle 268) from both longitudinal and latitudinal mechanical shocks.

It is noted that according to some embodiments, tip section 200 may include more than one side looking camera. In this case, the side looking cameras may be installed such that their fields of view are substantially opposing. However, different configurations and number of side looking cameras are possible within the general scope of the current specification.

Fluid channeling component 600 includes a side service channel 650 having a side service channel opening 350.

Reference is now made to FIG. 1, along with FIGS. 3A, 3B, 3C, and 3D which show a perspective view of a tip section 200 of a multi jet endoscope assembly 6501 comprising a plurality of side jets, in addition to a front jet, to enable improved flushing according to an embodiment of the present specification.

Figure 3A:
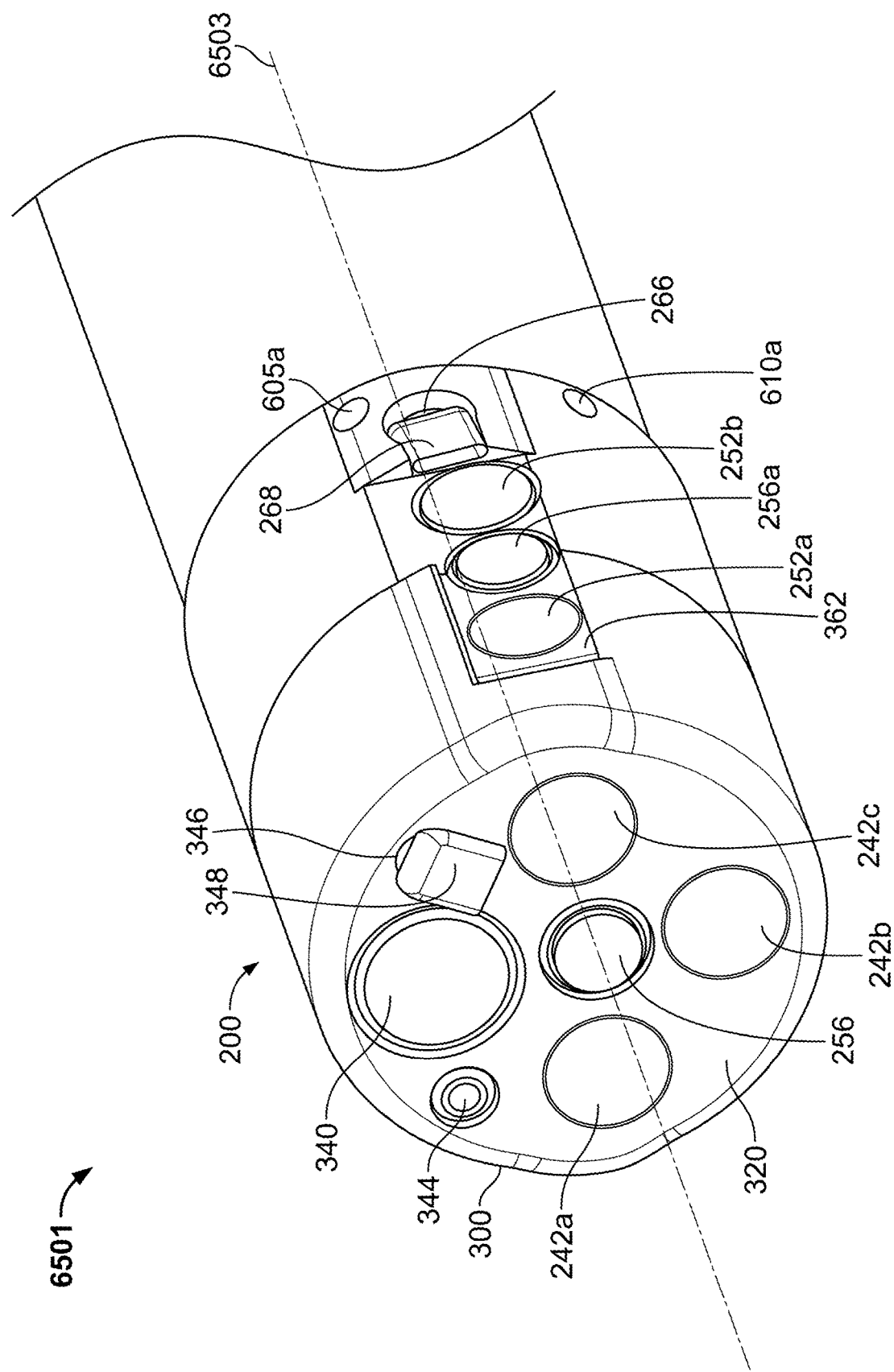
FIG. 3A illustrates a perspective view of a tip section of a multi jet endoscope assembly according to one embodiment of the present specification.
Figure 3D:
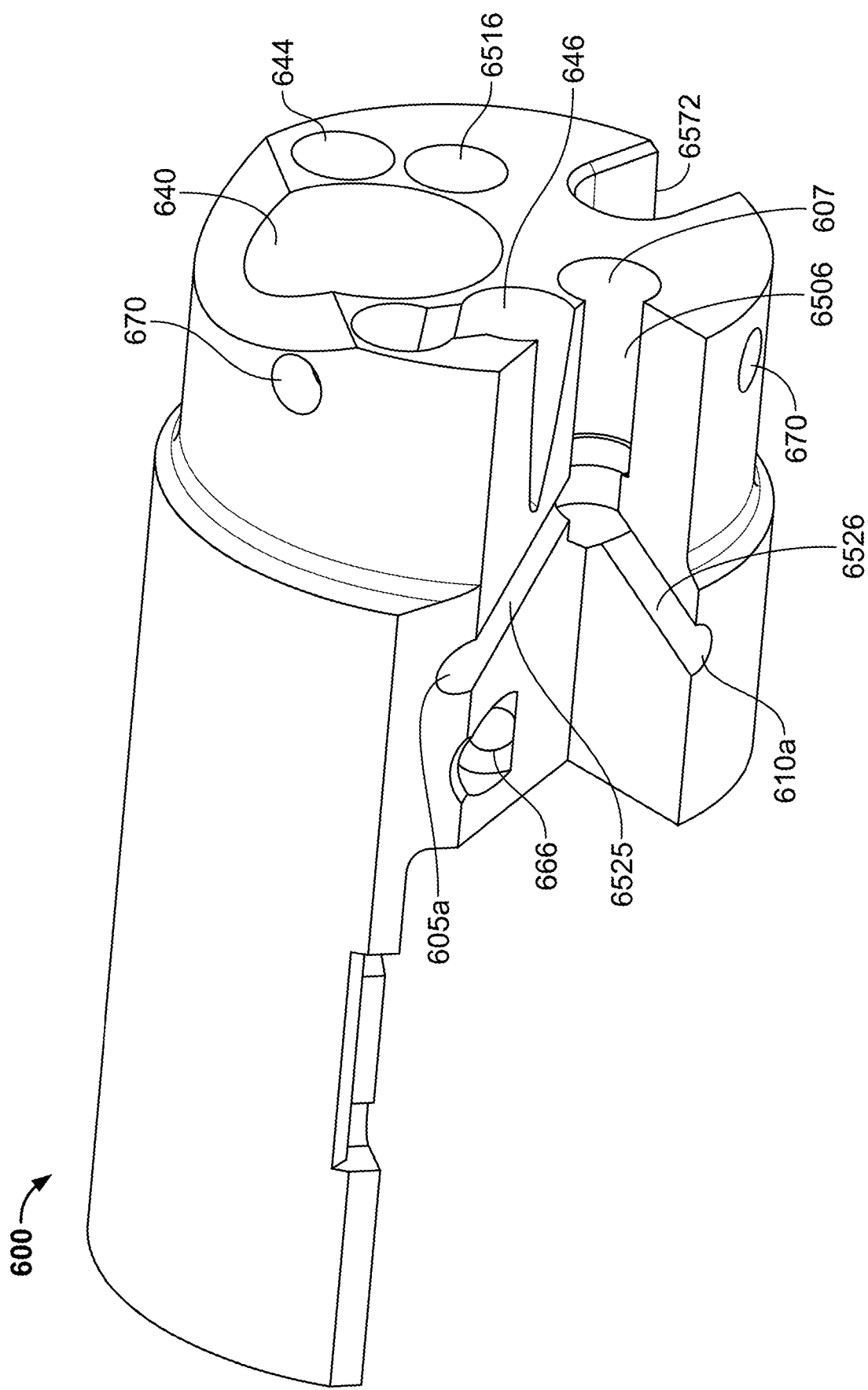
FIG. 3D illustrates a perspective view of a fluid channeling component of the multi jet endoscope assembly of FIG. 3A.

Tip cover 300 fits over the inner parts of the tip section 200 including electronic circuit board assembly 400 (shown in FIG. 1) and fluid channeling component 600 (shown in FIG. 3D) and to provide protection to the internal components in the inner parts. Holes 670 for pins for tip cover 300 are provided on fluid channeling component 600, as shown in FIG. 3D. Further, FIG. 3D shows a groove 6572 for an electrical cable. Tip cover 300 includes a front panel 320 having a transparent surface, window, or opening for front optical lens assembly 256, of front looking camera or viewing element 116, along with optical windows 242a, 242b and 242c of illuminators 240a, 240b and 240c, respectively.

The front panel 320 includes a working channel opening 340 of a working channel 640 and jet channel opening 344 of jet channel 644. Jet channel 644 is configured for providing a high-pressure jet of fluid, such as water or saline, for cleaning the walls of the body cavity. Also located on front panel 320 of tip cover 300 is injector opening 346 of injector channel 646 having a nozzle 348 aimed at front optical lens assembly 256. Injector channel 646 is configured for injecting fluid (liquid and/or gas) to wash contaminants such as blood, feces and other debris from a surface of front optical lens assembly 256 of front looking camera or viewing element 116. Optionally, injector channel 646 may be configured for cleaning at least a surface of front optical lens assembly 256 and one, two, or all of optical windows 242a, 242b and 242c. Injector channel 646 is fed by fluid such as water and/or gas which may be used for cleaning and/or inflating a body cavity. In one embodiment, the optical axis of the front looking camera or viewing element 116 is essentially directed along the central longitudinal axis 6503 that runs through the long dimension of the tip of the endoscope 6501.

FIG. 3B shows sidewall 362 of tip cover 300 comprising a transparent surface, window, or opening to side optical lens assembly 256a for a side looking viewing element, which may be similar to front optical lens assembly 256, and optical windows 252a and 252b of illuminators for the side looking viewing element. Also, as shown in FIG. 3C, the sidewall 362 of tip cover 300 on the opposing side to side optical lens assembly 256a is an optical lens assembly 256b for side looking viewing element 116b, and optical windows 252a and 252b of corresponding illuminators for side looking viewing element 116b. In one embodiment, the optical axis of one or both of the side looking viewing elements or cameras are essentially perpendicular to the optical axis (which is along the central longitudinal axis 6503 of the endoscope) of the front looking viewing element 116. In one embodiment, the optical axis of one or both of the side looking viewing elements forms an obtuse angle with the optical axis of the front viewing element 116 while in an alternate embodiment, the optical axis of one or both of the side viewing elements forms an acute angle with the optical axis of the front viewing element 116.

In addition, side injector openings 266 of corresponding side injector channels 666 are located at respective distal ends of the opposing sidewalls 362 as shown in FIGS. 3B and 3C. Nozzle covers 267 may be configured to fit the corresponding side injector openings 266. The nozzle covers include nozzles 268 that are aimed at side optical lens assemblies 256a, 256b and configured for injecting fluid to wash contaminants such as blood, feces and other debris from at least a surface of side optical lens assemblies 256a, 256b of the side looking viewing elements. The fluid may include gas which may be used for inflating a body cavity. Optionally, nozzles 268 may be configured for cleaning the side optical lens assembly and both optical windows on the opposing sides of the tip 200.

According to some embodiments, side injector channels 666 may be configured to supply fluids for cleaning any of the tip elements (such as any optical assembly, optical lens assembly, windows, illuminators, and other elements). Optionally, injector channel 646 and side injector channels 666 may be fed from the same channel.

As shown in FIGS. 3A through 3D, in accordance with an embodiment, two side jet openings 605a, 610a, fed by a common side jet channel 6506, are provided around the side periphery at the proximal end of the tip 200. Thus, the two side jet openings 605a, 610a which are fed by common side jet channel 6506 form a Y-shaped fluid conduit, described in greater detail below. The manifold shown in FIG. 3D includes a housing having a partially cylindrical shape with a curved top surface, a partially curved first side and a partially curved second side, wherein manifold housing is formed from a base portion with a first width, a first length, and a proximal surface and an elongated portion, which is attached to the base portion, with a second width, a second length, and a distal surface, wherein the first width is greater than the second width and the first length is less than the second length. A first channel 640 extends from the base portion through the elongated portion, wherein the first channel 640 has an entrance port positioned on said proximal surface of the base portion and an exit port positioned on a distal surface of the elongated portion. A second channel 644 extends from the base portion through the elongated portion, wherein the second channel 644 has an entrance port positioned on said proximal surface of the base portion and an exit port positioned on a distal surface of the elongated portion.

The Y-shaped fluid conduit comprises a central stem portion or common side jet channel 6506, a first prong portion 6525, and a second prong portion 6526, wherein the central stem portion 6506 extends from an entrance port 607 on the proximal surface of the base portion through the base portion, wherein the first prong portion 6525 extends from an end of the central portion through the base portion to an exit port on the partially curved first side; and wherein the second prong portion 6526 extends from an end of the central portion through the base portion to an exit port on the partially curved second side. In one embodiment, the exit port extending from the first prong portion 6525 forms side jet opening 605a while the exit port extending from the second prong portion 6526 forms side jet opening 610a.

A third channel 646 extends from an entrance port on the proximal surface of the base portion through to an exit port on the partially curved first side. A fourth channel 6516 extends from an entrance port on the proximal surface of the base portion through to an exit port on the partially curved second side. Each of the first, second, third, and fourth channels are fluidically isolated and separated from each other.

The common side jet channel 6506 has an entry port 607 at a proximal end of the fluid channeling component 600. Similarly, two side jet openings 605b, 610b, fed by another common side jet channel, are provided on the opposite side of side jet openings 605a and 610a. In one embodiment the two side jet openings 605a, 605b, 610a, 610b on either side of the tip are positioned in such a way that the side injector openings 266 (one on both sides of the tip) are situated between them. Additionally, in one embodiment, the two side jet openings 605a, 605b, 610a, 610b on either side of the tip are positioned close to the side optical lens assemblies 256a, 256b of the side looking cameras (on both sides of the tip) such that when fluid is ejected from the side jet openings it is propelled at an approximately 45 degree angle and past the cameras, so that a physician can see the fluid being expelled. The fluid can be water or saline.

It should be noted that, in alternate embodiments, side jet openings can be configured around the side periphery in any suitable number, including 2, 4, 6, or 8. Also, the side jet openings can have a plurality of angular configurations causing fluid to exit at different angles relative to a lateral plane that includes the side optical lens assemblies of side viewing elements and the optical windows of the corresponding illuminators but not the front optical lens assembly of the front viewing element. In one embodiment, the optical axis of the side viewing elements is perpendicular to the lateral plane as well as the optical axis of the front viewing element which is along the central longitudinal axis 6503 of the endoscope. These angles of fluid exit can range from 45 to 60 degrees or 120 to 135 degrees relative to the lateral plane. Acute angles of exit of 45 to 60 degrees enable fluid to be expelled in the direction of movement of the endoscope while obtuse angles of exit of 120 to 135 degrees enable fluid to be expelled in the direction opposite to the direction of movement of the endoscope, thereby aiding the endoscope movement within a body cavity. This is because, if the jet is directed in an opposite direction of movement of the endoscope, the resistance of the colon walls may push the scope forward like a jet engine.

In accordance with one embodiment, the side jet openings are positioned at a distance ranging from 5 to 10 millimeters, and preferably 8.5 to 9.5 millimeters from the side optical lens assemblies on the circumference of the endoscope such that the fluid exiting the openings form angles ranging from 50 degrees to 60 degrees relative to a lateral plane containing the side optical lens assemblies and corresponding side optical windows (but not containing front optical lens assembly of the front viewing element). Also, the side jet openings have a diameter of about 1.4 to 1.7 millimeters, in one embodiment.

Referring now to FIG. 1 and FIGS. 3A through 3D, in an embodiment, a jet distributor is provided to supply fluids to each of the side jet openings, such as 605a, 605b, 610a, 610b in the multi jet endoscope tip 6501 of FIGS. 3A through 3D, and the front jet 344. The jet distributor typically comprises three fluid channels to provide fluid to the front jet 344, right-side-jets 605a, 610a and left-side-jets 605b, 610b in the endoscope tip 6501.

Figure 4:
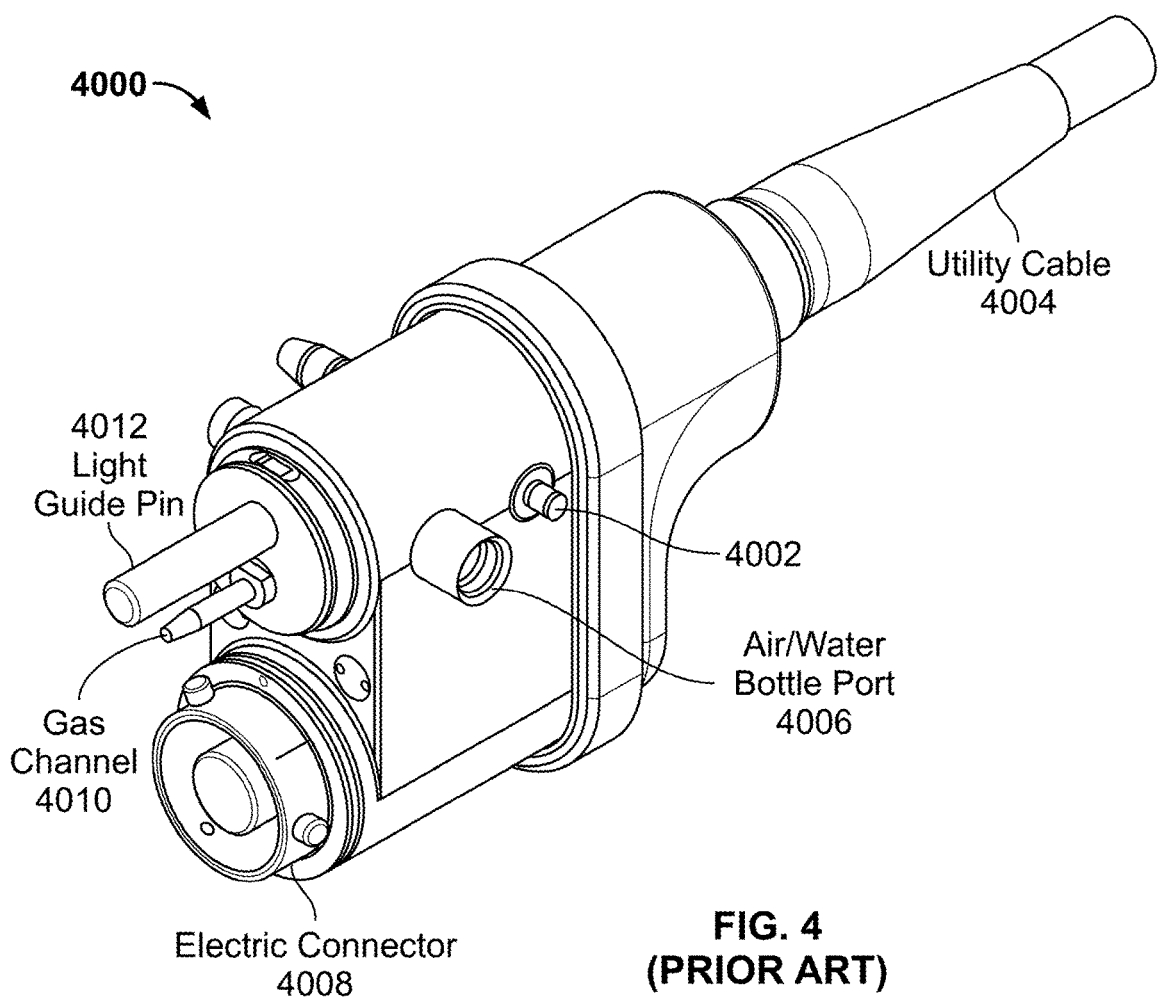
FIG. 4 illustrates an exemplary main connector, which is known in the prior art.

FIG. 4 illustrates an exemplary embodiment of a main connector 4000, which is known in the prior art. A jet connector port 4002 is adapted for use with an endoscope that includes multiple jets. In embodiments, jet connector port (also referred to as an auxiliary water supply port) 4002 has more than one channel opening to enable jet flow to a front jet and at least one side jet of the multi-jet endoscope. The jet channels are located within a utility cable 4004 and are used to channel fluids there through and towards the respective front and side jet openings in the distal tip of the multi jet endoscope. In embodiments, a water bottle port (a water connector) 4006, is attached to a water supply, such as a water bottle or hospital facilities, to provide fluid to an insufflation and/or irrigation system placed within the endoscope tip. FIG. 4 illustrates other standard components of main connector 4000 that are provided, including an electric connector 4008 to connect the system to a source of electricity and therefore supply power to operate electric and electronic components of main connector 4000. A gas channel 4010 may provide gas flow to the tip of the endoscope. An elongated protruding member 4012 is also shown, which may be adapted to fit into a receiving structure present on the surface of a main control unit.

Figure 5A:
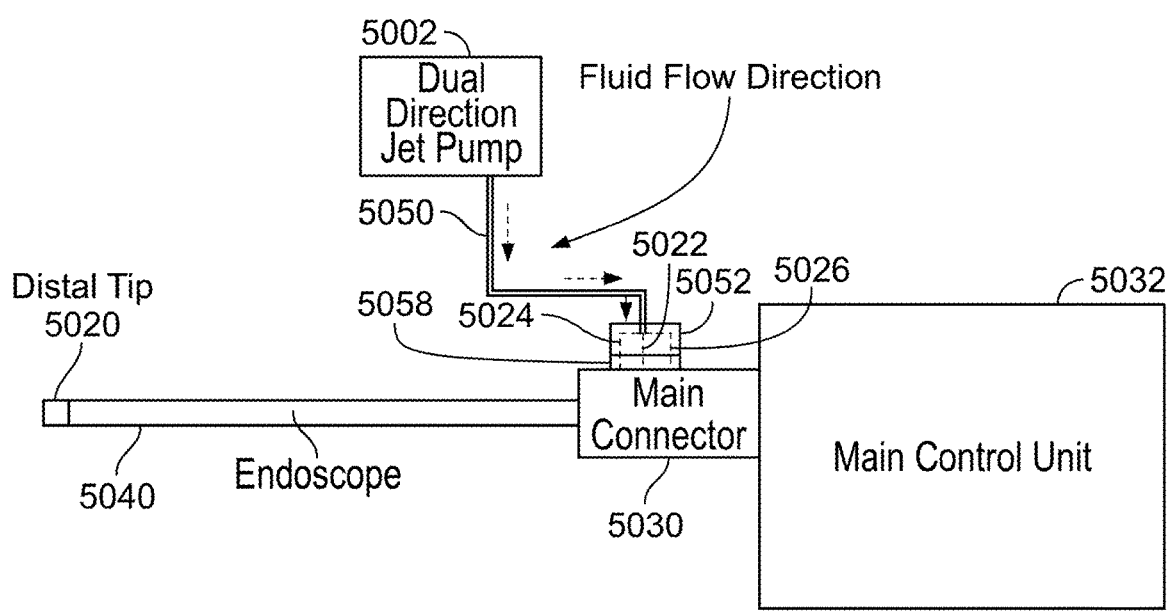
FIG. 5A illustrates an embodiment where a dual-direction jet pump enables fluid flow through a single pipeline tube to a main connector, in accordance with an embodiment of the present specification.
Figure 5B:
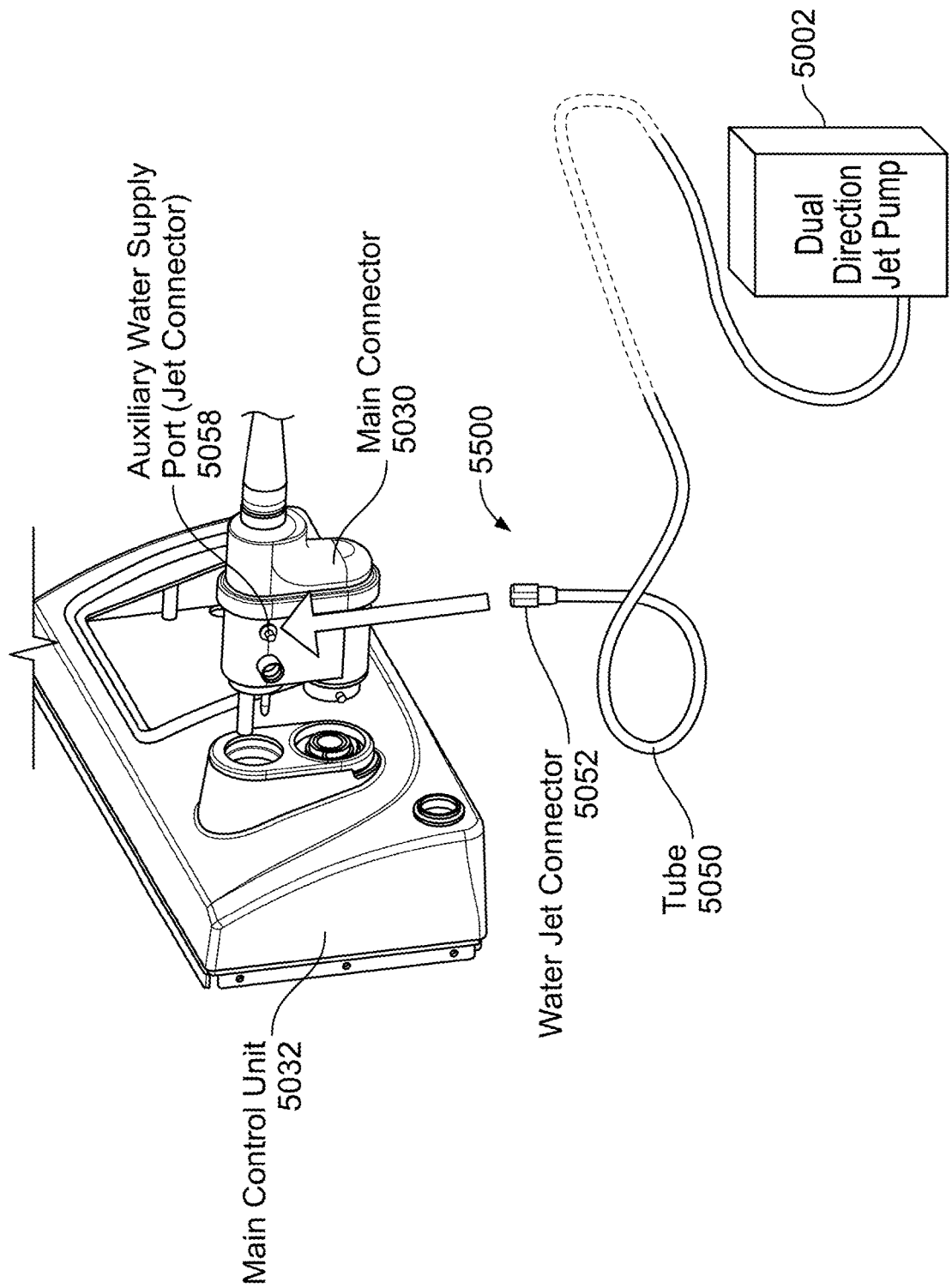
FIG. 5B illustrates an exemplary coupling system, in accordance with an embodiment of the present specification.

Referring to FIGS. 5A and 5B, in an embodiment, a dual direction jet pump 5002 is located external to an endoscope 5040 and is connected to a main control unit 5032 of endoscope 5040. In an embodiment, pump 5002 is connected to a main connector 5030 at a jet connector port 5058. In an embodiment, jet connector port 5058 is similar to jet connector port 4002 described in context of FIG. 4. FIG. 5A illustrates an embodiment where dual-direction jet pump 5002 enables control of fluid flow through a tube 5050 to main connector 5030. In embodiments, the single fluid flow-path enables fluid to travel through multiple fluid channels including a front jet channel and/or side-jet channel for dispersion through a front jet opening and/or side jet opening that is located on the front panel and the side panel of a distal tip 5020 of endoscope 5040, respectively. In embodiments, a first combination of fluid channels and a second combination of fluid channels are co-linearly placed within tube 5050. In an embodiment, the first combination of fluid channels is connected to the front jet channel within the endoscope, which leads to the front jet opening. Similarly, the second combination of fluid channels is connected to the front-jet channel as well as the side-jet channels within the endoscope, which lead to the front-jet opening and the one or more side-jet openings.

As illustrated, in an embodiment, dual-direction jet pump 5002 supplies fluid to three jet openings in jet connector port 5058 of endoscope 5040 via at least three exiting pipelines 5022, 5024, and 5026, of which pipelines 5024 and 5026 connect to side jet channels for fluid dispersion through two side jet openings located on the side-walls of distal tip 5020. Pipeline 5022 connects to a front jet channel for fluid dispersion through a front jet opening on the front face of distal tip 5020. Hence, in the embodiment illustrated in FIG. 5A, a single pump 5002 enables controlled flow of fluid through either a front jet or the front jet and the side jets.

Dual direction jet pump 5002 may connect to main control unit 5032 at port 5058, by using a coupling system. FIG. 5B illustrates an exemplary coupling system 5500, in accordance with an embodiment of the present specification. In accordance with an embodiment of the present specification, coupling system 5500 comprises a water jet connector 5052, which provides a coupling mechanism between port 5058 and tube 5050. Tube 5050 connects to water jet connector 5052 and dual direction jet pump 5002. In one embodiment, connector 5052 is a luer connector, or any other type of connector that enables connecting system of small-scale fluid fittings used for making leak-free connections between a male-taper fitting and its mating female part on medical instruments.

Figure 5C:
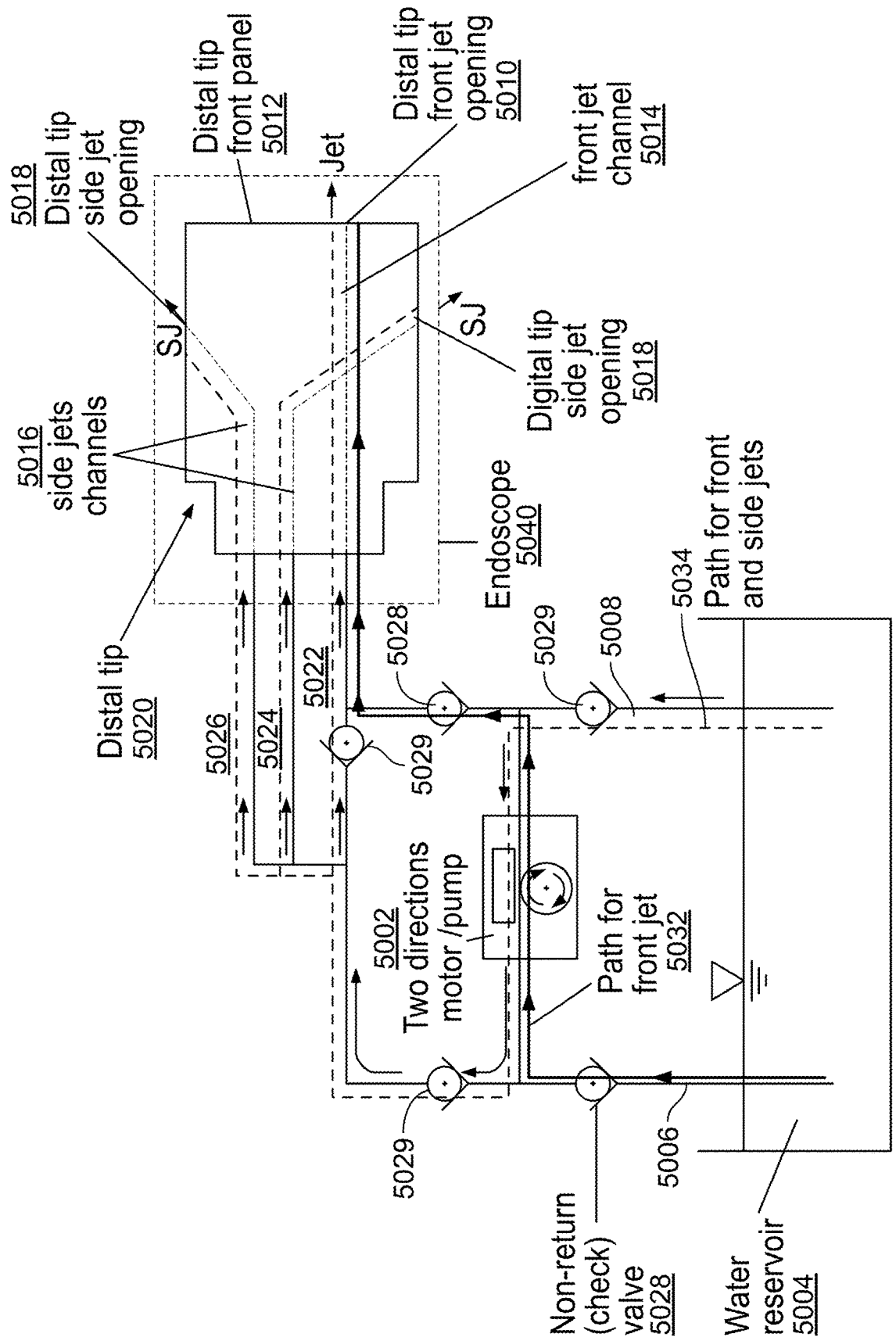
FIG. 5C is a block diagram illustrating connection between a dual-direction jet pump and an endoscope, in accordance with an embodiment of the present specification.

FIG. 5C is a block diagram illustrating a connection between a dual-direction jet pump and an endoscope 5040, in accordance with an embodiment of the present specification. In embodiments, dual-direction jet pump includes a pump, such as jet pump 5002. Jet pump 5002 pumps fluid from a fluid source such as a water reservoir 5004, via at least two fluid pipelines 5006 and 5008. In an embodiment, pipelines 5006 and 5008 are adjacently placed within single tube, conduit or pipeline 5050. In embodiments, pipeline 5006 forms a part of the first combination of fluid channels that supply fluid to front jet opening 5010, and pipeline 5008 forms a part of the second combination of fluid channels that supply fluid to front jet opening 5010 and side jet openings 5018.

In embodiments, a first fluid pipeline 5006 provides a path for pumping water for a front jet through a front jet channel 5014 and via a front jet opening 5010 on a front panel 5012 of a distal tip 5020 of endoscope 5040. Water pumped by pump 5002 through first fluid pipeline 5006 may be directed through a front jet channel 5014 to be dispersed from front jet opening 5010. FIG. 5C illustrates a fluid path 5032 corresponding to the first combination of fluid channels, for fluid to flow towards front jet opening 5010. Path 5032 is shown in the form of a thick line, through pipeline 5006, via pump 5002, through channel 5014, towards distal tip front jet opening 5010.

In embodiments, a second fluid pipeline 5008 provides a path for pumping water for a front and one or more side jets of the endoscope. FIG. 5C illustrates a fluid path 5034 corresponding to the second combination of fluid channels, for fluid to flow towards front jet opening 5010 and one or more side jet openings 5018, of endoscope 5040. Path 5034 is shown in the form of a thick dashed line, through pipeline 5008, via pump 5002, towards distal tip front jet opening 5010 and side jet openings 5018. Water pumped through the second fluid pipeline 5008 may travel through front jet channel 5014 and side jet channels 5016, for dispersion through front jet opening 5010 and one or more distal tip side jet openings 5018. Jet openings 5010 and 5018 are located within distal tip 5020 of the endoscope.

Pump 5002 is a dual-direction pump adapted to direct the fluid jet's flow to the front jet, to one or more of the side jets, or to both the front and side jets concurrently. The fluid is supplied by pump 5002 to three jet openings in tip 5020 of endoscope 5040 via three fluid pipelines 5022, 5024, and 5026. In an embodiment, each of the three exiting fluid pipelines 5022, 5024, and 5026 supply fluid to a fluid channel positioned within tip 5020. In an embodiment, pipelines 5024 and 5026 supply fluid to side jet channels 5016; and pipeline 5022 supplies fluid to front jet channel 5014.

In an embodiment, the three exiting fluid pipelines 5022, 5024, and 5026 are located within tube 5050 that includes pipelines 5006 and 5008. In an embodiment, pipeline 5008, which provides the path for fluid to travel to front and side jet openings 5010 and 5018, is connected to at least two or more pipelines that branch out from pipeline 5008. In the figure, pipeline 5008 is shown to branch out in to pipelines 5022, 5024, and 5026. In embodiments, pipelines 5022, 5024, and 5026 are parallel pipelines. Pipeline 5022 is connected to front jet channel 5014, and pipelines 5024 and 5026 are connected to side jet channels 5016. In embodiments, pipeline 5006 also merges with pipeline 5022, in order to connect subsequently with front jet channel 5014. In embodiments, pipelines 5022, 5024, and 5026 connect with their corresponding channels through a main connector (shown in FIG. 5B). The three pipelines 5022, 5024, and 5026 are embedded within tube 5050 (shown in FIGS. 5A and 5B) along connector 5052 (shown in FIGS. 5A and 5B). Pipelines 5022, 5024, and 5026 are aligned into the associated channels in connector port 5058 (shown in FIGS. 5A and 5B). The main connector is also coupled with a controller unit that acts as a main control unit for the endoscope.

In various embodiments, in order to activate the jet and wash a lumen in a patient's body, a user/physician operating endoscope 5040 may use an activation system such as, but not limited to, a button located either on a handle of the endoscope, on the main control unit, or on a control panel of the endoscope, that, when pressed, causes a controller to activate the pump, thereby causing water to flow in one of two directions or to shut off. For example, once the button on an endoscope is pressed, a controller, which is in data communication with the button, causes the dual-direction jet pump 5002 to start providing fluid at a pre-determined rate to one of, two of, or each of the three fluid channels 5022, 5024, and 5026, of the endoscope. In another embodiment, pushing the button once may activate the pump in order to apply pressure to the fluid through pipeline 5006 and supply fluid to the front jet. In this embodiment, pushing the button twice may cause a controller to activate the pump in order to apply pressure to the fluid through pipeline 5008 and supply fluid to the front jet and the side jets. In another embodiment, the user/physician may be required to step on a foot pedal to cause a controller to activate jet-pump 5002. Thus, in embodiments, two direction motor/pump 5002 is operated by a pushed button, a lever, or any other known trigger, or activation, mechanism to cause the fluid to flow through one, two, and/or all three fluid channels and pressing the activation mechanism a predetermined number of times corresponds with causing fluid to flow through a specific one or combination of the fluid channels. During operation of embodiments of the present specification, the user selects an option to either supply fluid through front jet opening 5010, or through front jet opening 5010 and side jet opening 5018.

If the user choses to supply fluid to only front jet opening 5010, pump 5002 is activated to apply pressure to fluid through pipeline 5006. In an embodiment, a series of non-return check valves 5028 are placed along path 5032, which are also activated in order to control the operation. Each check valve 5028 ensures that fluid flows through the pipeline in one direction only. Pump 5002 pumps fluid in the direction indicated by path 5032 in order to supply fluid to front jet opening 5010. A first valve 5028 may be located in pipeline 5006 between reservoir 5004 and pump 5002 that ensures the fluid flows in the desired direction of path 5032. A second check valve 5028 may be located between pump 5002 and pipeline 5022 that is connected to front jet channel 5014. Second valve 508 also ensures that fluid flows in the direction of path 5032, while pump 5002 pumps fluid from pipeline 5006 in the same direction.

Alternatively, if the user choses to supply fluid to front jet opening 5010 and side jet openings 5018 simultaneously, pump 5002 is activated to pump fluid through pipeline 5008 in a direction that is opposite to the direction for pipeline 5006. A series of non-return check valves 5029 ensure that the fluid flows in the direction of path 5034 for supplying fluid to front and side jet openings 5010, 5018. In some embodiments, a first check valve 5029 is placed between reservoir 5004 and pump 5002 along pipeline 5008. A second check valve 5029 may be placed along pipeline 5008 between pump 5002 and before the point where pipeline 5008 branches out to pipelines 5022, 5024, and 5026.

Figure 5D:
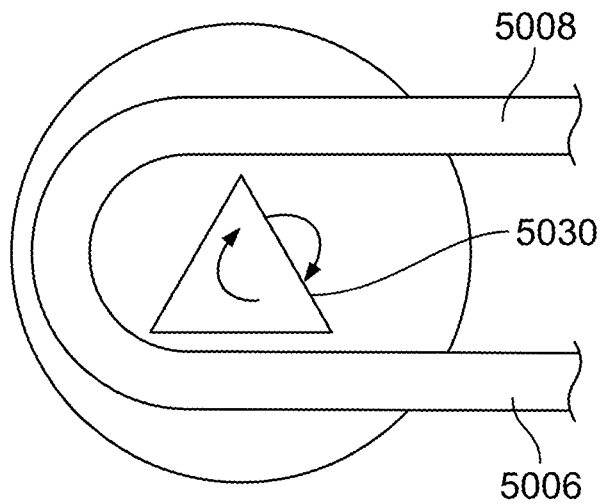
FIG. 5D illustrates an exemplary operation of dual direction pump, in accordance with an embodiment of the present specification.

FIG. 5D illustrates an exemplary operation of dual direction pump 5002, in accordance with an embodiment of the present specification. In embodiments, pump 5002 is a peristaltic pump, which operates on the basis of alternating compression and relaxation of a tube. Pipelines 5006 and 5008 may form a single continuous tube that is wound around a rotating shoe or roller 5030. Rotating shoe or roller 5030 forms pump 5002. Roller 5030 passes along the length of the tube, resulting in two ends of the tube that are on the two sides of roller 5030. These two ends may form the two paths 5032 (corresponding to pipeline 5006) and 5034 (corresponding to pipeline 5008). During operation, roller 5030 compresses the tube and creates a seal between the two sides of the tube, such that fluid is suctioned through the selected one of the two paths 5006 and 5008. Rotation of roller 5030 in one direction may pull fluid through one path, while rotation of roller 5030 in an opposite direction may pull the fluid through the other path. Therefore, operating in one direction may supply fluids to front and side jets, while operating in the other direction may supply fluids to the front jet only. In embodiments, a single trigger mechanism (single button, lever, pedal, or any other) may be toggled to change the direction of pump 5002.

Figure 6:
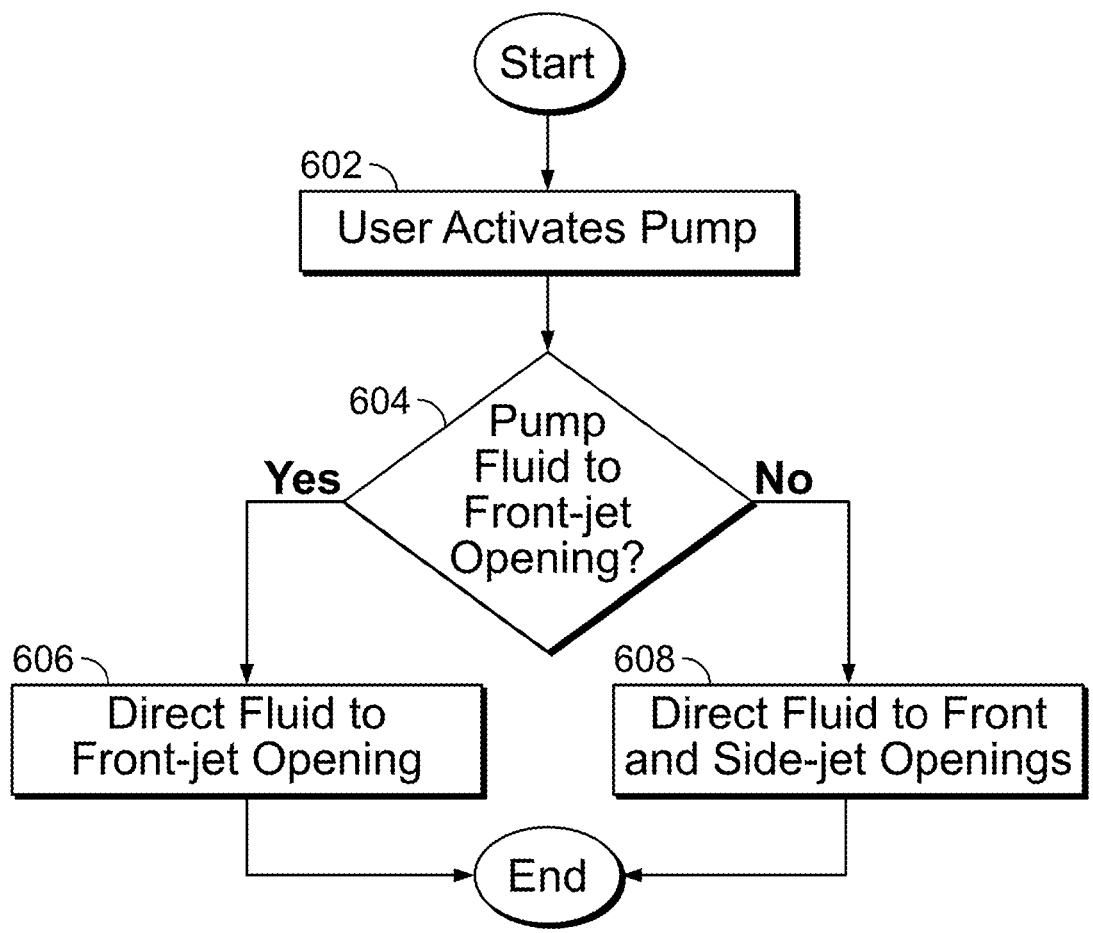
FIG. 6 is a flow chart illustrating an exemplary method of controlling a flow direction of fluid from a source external to an endoscope into a plurality of fluid channels positioned within the endoscope, in accordance with an embodiment of the present specification.

FIG. 6 is a flow chart illustrating an exemplary method of controlling a flow direction of fluid from a source external to an endoscope into a plurality of fluid channels positioned within the endoscope. Simultaneously referring to FIGS. 5A, 5B, and 5C, at step 602, the user activates pump 5002 connected to tube 5050. In embodiments, tube 5050 includes the first and second combinations of fluid channels that are collinearly placed within tube 5050. The first combination of fluid channels, corresponding to path 5032, direct fluid to front-jet opening 5010; whereas the second combination of fluid channels, corresponding to path 5034, direct fluid to front jet opening 5010 and side-jet openings 5018. Therefore, at step 604, the system determines whether the user has activated the pump to direct fluid to front-jet opening 5010 only or to front-jet opening 5010 and side-jet openings 5018 simultaneously. If the user has activated the first option, at 606, the fluid is directed by pump 5002 via path 5032 comprising the first combination of fluid channels, to front-jet channel 5014. Alternatively, if the user has activated the second option, at 608, the fluid is directed by pump 5002 via path 5034 comprising the second combination of fluid channels, to front-jet channel 5014 and a side-jet channels 5016.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An apparatus for controlling a flow direction of fluid from a fluid source external to a medical device into a plurality of fluid channels positioned in the medical device, comprising:
   a tube comprising a first combination of fluid channels and a second combination of fluid channels;
   a pump connected to the tube, wherein the pump is adapted to direct fluid from the fluid source to the first combination of fluid channels and the second combination of fluid channels in the tube; and
   a controller to activate the pump, wherein the controller is configured to cause the pump to direct fluid to the first combination of fluid channels upon a first activation of the controller, and wherein the controller is configured to cause the pump to direct fluid to the second combination of fluid channels upon a second activation of the controller;
   wherein the first combination of fluid channels is configured to supply fluid to a first opening of the medical device;
   wherein the second combination of fluid channels is configured to supply fluid to a second opening positioned at the distal end of the medical device;
   wherein the pump is configured to direct fluid in a first direction through the first combination of fluid channels upon the first activation of the controller, wherein the pump is configured to direct fluid in a second direction through the second combination of fluid channels upon the second activation of the controller, and wherein the first direction is different from the second direction;
   wherein the first combination of fluid channels comprises:
      a first fluid channel extending from a fluid source to a first channel end;
      a second fluid channel extending from the first channel end through a first port of the pump and a second port of the pump to a second channel end, wherein the second fluid channel is fluidically connected to the first fluid channel, and
      a third fluid channel extending from the second channel end to a third channel end, wherein the third channel end is configured to couple with a fourth channel of the medical device, and wherein the fourth channel is fluidically coupled to the first opening.

2. The apparatus of claim 1, wherein the second combination of fluid channels comprises:
   a fifth fluid channel extending from the fluid source to the second channel end, wherein the fifth fluid channel is fluidically coupled to the second fluid channel, and
   a sixth fluid channel extending from the first channel end to a fourth channel end, wherein the fourth channel end is configured to couple with a seventh fluid channel of the medical device, and wherein the seventh channel is fluidically coupled to the second opening.

3. The apparatus of claim 2, further comprising a first check valve in the first fluid channel and a second check valve in the fifth fluid channel.

4. The apparatus of claim 1, further comprising a user trigger to control the controller, wherein the user trigger comprises a button, and wherein the button is configured such that pressing the button causes the first activation of the controller and pressing the button twice causes the second activation of the controller.

5. The apparatus of claim 1, wherein the first combination of fluid channels and the second combination of fluid channels are configured to fluidically connect to a proximal portion of the medical device.

6. The apparatus of claim 1, wherein the second combination of fluid channels is configured to supply fluid to the first opening, the second opening, and a third opening of the medical device, wherein a central longitudinal axis of the third opening is angled relative to the central longitudinal axis of the medical device.

7. The apparatus of claim 1, wherein the pump is a peristaltic pump.

8. The apparatus of claim 1, further comprising a user trigger to control the controller, wherein the user trigger comprises a button, and wherein the button is configured such that pressing the button causes the first activation of the controller and pressing the button twice causes the second activation of the controller.

9. The apparatus of claim 1, further comprising a user trigger to control the controller, wherein the user trigger comprises a lever, and wherein the lever is configured such that pulling the lever causes the first activation of the controller and pushing the lever causes the second activation of the controller.

10. The apparatus of claim 1, further comprising a user trigger to control the controller, wherein the user trigger comprises a pedal, and wherein the pedal is configured such that stepping on the pedal causes the first activation of the controller and stepping on the pedal twice causes the second activation of the controller.

11. The apparatus of claim 1, wherein the first combination of fluid channels and the second combination of fluid channels are co-linearly placed within the tube.

12. The apparatus of claim 1, wherein the first opening is a front opening in a distal tip of the medical device.

13. The apparatus of claim 1, wherein the second opening is a side opening in a distal tip of the medical device.

14. The apparatus of claim 1, further comprising a first check valve in the first fluid channel, and a second check valve in the third fluid channel.

\* \* \* \* \*